(12) United States Patent
Tsuchida et al.

(10) Patent No.: US 11,069,903 B2
(45) Date of Patent: Jul. 20, 2021

(54) METAL PARTICLE SUPPORTED CATALYSTS, METHODS FOR PRODUCING SAME, AND FUEL CELLS USING SAME

(71) Applicant: Panasonic Intellectual Property Management Co., Ltd., Osaka (JP)

(72) Inventors: Shuzo Tsuchida, Nara (JP); Ryouhei Seki, Osaka (JP); Yasuhiro Ueyama, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 254 days.

(21) Appl. No.: 15/797,336

(22) Filed: Oct. 30, 2017

(65) Prior Publication Data
US 2018/0159145 A1 Jun. 7, 2018

(30) Foreign Application Priority Data
Dec. 5, 2016 (JP) .............................. JP2016-235630

(51) Int. Cl.
| | | |
|---|---|---|
| H01M 4/92 | (2006.01) | |
| H01M 4/86 | (2006.01) | |
| B01J 23/42 | (2006.01) | |
| H01M 8/1039 | (2016.01) | |
| C07C 309/06 | (2006.01) | |

(52) U.S. Cl.
CPC ............ *H01M 4/925* (2013.01); *B01J 23/42* (2013.01); *H01M 4/8663* (2013.01); *H01M 8/1039* (2013.01); *C07C 309/06* (2013.01)

(58) Field of Classification Search
None
See application file for complete search history.

(56) References Cited

U.S. PATENT DOCUMENTS

| | | | |
|---|---|---|---|
| 2011/0104492 A1 | 5/2011 | Muhler et al. | |
| 2016/0072133 A1* | 3/2016 | Akizuki | B22F 9/02 429/482 |

FOREIGN PATENT DOCUMENTS

| | | |
|---|---|---|
| EP | 2 990 105 | 3/2016 |
| JP | 2011-526331 | 10/2011 |
| JP | 2012-129059 | 7/2012 |
| JP | 2013-196983 | 9/2013 |

(Continued)

OTHER PUBLICATIONS

Google translation of JP5386977; Aug. 17, 2020.*

(Continued)

*Primary Examiner* — Guinever S Gregorio
(74) *Attorney, Agent, or Firm* — Wenderoth, Lind & Ponack, L. L.P.

(57) ABSTRACT

A catalyst, includes: a carbon support that possesses functional groups including a carboxyl group; and a metal that is supported onto the carbon support, wherein the proportion of the carboxyl group to the functional groups is 10% or higher. A method for producing a catalyst includes: (i) supporting metal particles onto a carbon support; (ii) bringing the carbon support into contact with an acid solution; and (iii) calcining the carbon support after Step (ii), wherein the carbon support included in the produced catalyst possesses functional groups including a carboxyl group, and the proportion of said carboxyl group to the functional groups is 10% or higher.

3 Claims, 8 Drawing Sheets

(56) References Cited

FOREIGN PATENT DOCUMENTS

WO    2014/175099    10/2014

OTHER PUBLICATIONS

Extended European Search Report dated Feb. 9, 2018 in European Application No. 17196058.6.
Jha et al.: "Functionalized Single-Walled Carbon Nanotube-Based Fuel Cell Benchmarked Against US DOE 2017 Technical Targets", Scientific Reports, vol. 3, No. 2257, pp. 1-7 (2013).

* cited by examiner

PRIOR ART

METAL PARTICLE SUPPORTED CATALYSTS, METHODS FOR PRODUCING SAME, AND FUEL CELLS USING SAME

TECHNICAL FIELD

The technical field relates to metal particle supported catalysts, methods for producing the same, and fuel cells using the same. In particular, the technical field relates to metal particle supported, catalyst including platinum, methods for producing the same, and fuel cells using the same.

BACKGROUND

In recent years, with the popularization of fuel cells, there has been increasingly strong demand for reducing catalyst costs for polymer electrolyte fuel cells.

Therefore, manufacturers have conducted studies on various improvements, and have aimed at employing platinum more efficiently to improve power generation performance.

Among the studies conducted by manufacturers, the following technology has been developed. For example, carbon materials having few irregularities on their surfaces are employed as materials on which metal particles are supported. Accordingly, protons ($H^+$) required for power generation can easily conduct, and thus, the proton conduction overvoltage that serves as a resistance component is reduced to thereby improve power generation performance (JP-A-2012-129059).

The disclosure of JP-A-2012-129059 will be described with reference to FIGS. 8A (prior art) and 8B (prior art). In FIG. 8A (prior art), a carbon support 131 has large surface irregularities, and metal particles 132 are supported on the surface. A proton-conducting solid polymer material 133 (hereinafter, referred to as "ionomer") is further placed thereon. In this case, the proton-conducting solid polymer (ionomer) refers to a solid polymer material that protons can conduct through. For example, a perfluorocarbon sulfonic acid resin can be used.

However, since the carbon support 131 has large surface irregularities, protons are forced to travel correspondingly longer distances to conduct from the ionomer 133 to the metal particles 132. Consequently, the proton conduction overvoltage becomes higher. In order to solve such this problem, in JP-A-2012-129059, the carbon support 131 has smaller surface irregularities, distances between metal particles 132 and the ionomer 133 are reduced, to thereby cause a reduction in the proton conduction overvoltage, as shown in FIG. 8B (prior art).

SUMMARY

However, in cases in where carbon supports having smaller surface irregularities are used, as disclosed in JP-A-2012-129059, carbon supports having a smaller surface area would be a concern.

One concern when producing fuel cells is that it is required that the metal particle supported carbon materials (hereinafter, referred to as catalysts) are dispersed in water, a solvent, or a mixture thereof to prepare inks, and that the inks are coated onto electrolyte membranes. In that case, since the surface areas of carbon supports are smaller, amounts of water that are retained on the surfaces of the carbon supports are correspondingly reduced, and thus, the dispersion of the carbon materials would be difficult.

Another concern is that the surface areas of the carbon supports are smaller, metal particles supported onto the surfaces of the carbon supports are likely to come into close contact with each other, and thus, aggregations of the metal particles will occur. Consequently, a problem in which the metal particles are not efficiently employed for power generation in the fuel cells would arise.

Therefore, an object of the disclosure is to provide catalysts that makes it possible to reduce the proton conduction overvoltage, thereby improving power generation properties, even in cases in which carbon supports have large surface irregularities. Furthermore, another object of the disclosure is to provide methods for producing the catalysts. Still another object of the disclosure is to provide fuel cells using the catalysts.

In order to achieve the above-mentioned objectives, according to the first aspect of the disclosure, provided herein are catalysts, including: a carbon support that possesses functional groups including a carboxyl group; and a metal that is supported onto the carbon support, wherein the proportion of the carboxyl group to the functional groups is 10% or higher.

Moreover, according to the second aspect of the disclosure, provided herein are fuel cells, including the above-described catalysts; and an electrode layer containing an ionomer.

Furthermore, according to the third aspect of the disclosure, provided herein are methods for producing a catalyst, including: (i) supporting metal particles onto a carbon support; (ii) bringing the carbon support into contact with an acid solution; and (iii) calcining the carbon support after Step (ii), wherein the carbon support included in the produced catalyst possesses functional groups including a carboxyl group, and the proportion of said carboxyl group to the functional groups is 10% or higher.

According to the disclosure, it becomes possible to reduce the proton conduction overvoltage, thereby improving the power generation properties.

DESCRIPTION OF EMBODIMENTS

Hereinafter, embodiments of the disclosure will be described with reference to the drawings. Same or corresponding, parts will be referred to by same or similar reference symbols throughout the drawings, and overlapping descriptions therefor will be omitted below. In addition, although the disclosure will be described in detail below, the scope of the disclosure is not limited to the descriptions set forth below, and various modifications are carried out within the spirit of the disclosure and the scope of the appended claims.

Figure 1:
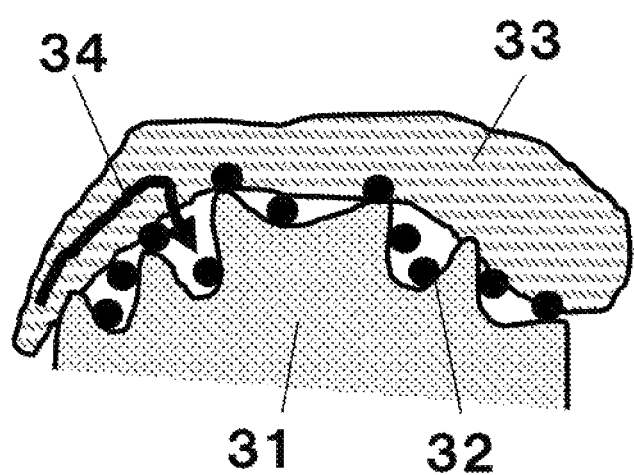
FIG. 1 is a diagram that shows a catalyst according to an embodiment.

FIG. 1 is a cross-section view of a catalyst according to one embodiment. The catalyst includes a carbon support 31, and metal particles 32 supported on the surface of the carbon support 31. An ionomer 33 (proton-conducting solid polymer material) is furthered placed thereon. In this case, the ionomer 33 may be a solid polymer material that protons are able to conduct through. For example, a perfluorocarbon sulfonic acid resin can be used therefor.

In the disclosure, the carbon support 31 has functional groups that differ from those found in conventional arts.

In addition, the carbon support 31 may have or may not have surface irregularities as found in the carbon support 131 in JP-A-2012-129059.

<Structure of Fuel Cell>

Figure 2:
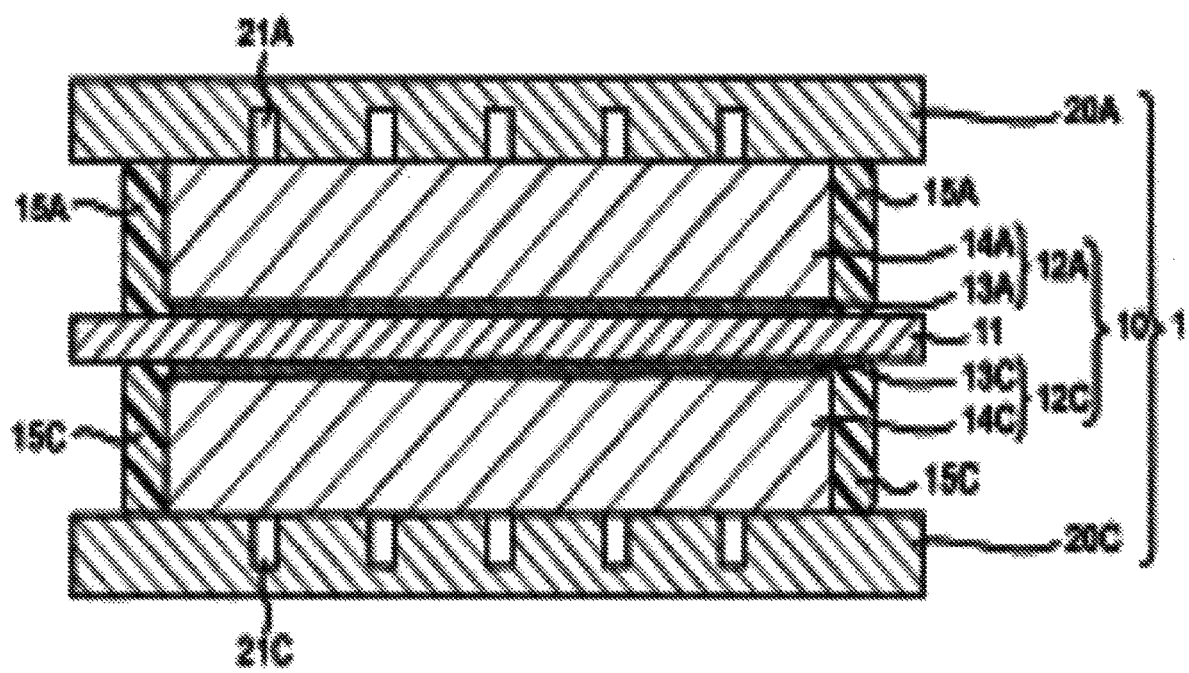
FIG. 2 is a diagram that shows a structure of a fuel cell according to an embodiment.

FIG. 2 is a cross-section view that shows one single cell that may be included in a fuel cell 5 according to the disclosure. In the fuel cell 5 according to the disclosure, a fuel gas containing hydrogen is caused to react with an oxidant gas containing oxygen (e.g., containing the air). Accordingly, the fuel cell 5 serves as a polymer electrolyte fuel cell that simultaneously produces electric power and heat. In addition, the fuel cell 5 according to the disclosure is not limited to such a polymer electrolyte fuel cell, and can be formed of various types of fuel cells.

As shown in FIG. 2, the fuel cell 5 includes a membrane electrode assembly (MEA) 10, and a pair of anode separators 20A and 20C that are placed on both sides, respectively, of the membrane electrode assembly 10. FIG. 2 shows only one single cell included in the fuel cell 5, and multiple cells having the same structure are stacked in the fuel cell 5.

Additionally, the stacked cells are preferably fastened at a predetermined fastening pressure by using a fastening member such as a bolt (not shown in the figure), in order to prevent leakage of the fuel gas and the oxidant gas, and in order to reduce contact resistance between them.

The membrane electrode assembly 10 includes a polymer electrolyte membrane 11 that selectively transports hydrogen ions, and a pair of electrode layers that are formed on both sides of the polymer electrolyte membrane 11, respectively. One of the electrode layers serves as an anode electrode 12A (also called a fuel electrode), and the other serves as a cathode electrode 12C (also called as an air electrode).

The anode electrode 12A includes (i) an anode catalyst layer 13A that is formed on one of the sides of the polymer electrolyte membrane 11 and contains as a main ingredient a carbon powder supported with a platinum group catalyst, and (ii) an anode gas diffusion layer 14A that is formed on the anode catalyst layer 13A and combines current collection effects and gas permeability.

The cathode electrode 12G includes (i) a cathode catalyst layer 13C that is formed on the other side of the polymer electrolyte membrane 11 and contains as a main ingredient a carbon powder supported with a platinum group catalyst, and (ii) a cathode gas diffusion layer 14C that is formed on the cathode catalyst layer 13C and combines current collection effects and gas permeability.

Fuel gas flow channels 21A, through each of which the fuel gas is caused to flow, are provided on a main surface of the anode separator 20A, which is located at the side where the anode electrode 12A is present. In this case, the main surface refers to a surface that comes into contact with the anode gas diffusion layer 14A.

For example, the fuel gas flow channels 21A may be formed as multiple grooves that are parallel to one another. Oxidant gas flow channels 21C, through each of which the oxidant gas is caused to flow, are provided on a main surface of the cathode separator 20C, which is located at the side where the cathode electrode 12C is present. In this case, the main surface refers to a surface that comes into contact with the cathode gas diffusion layer 14C.

The oxidant gas flow channels 21C may be formed as multiple grooves that are parallel to one another.

Additionally, on/in the anode separator 20A and the cathode separator 20C, a coolant flow channel (not shown in the figure) through which a cooling water or the like flows may be provided. Through the fuel gas flow channels 21A, the fuel gas is supplied to the anode electrode 12A, and, simultaneously, through the oxidant gas flow channels 21C, the oxidant gas is supplied to the cathode electrode 12C. Accordingly, reaction products produced on the anode electrode 12A and the cathode electrode 12C cause an electrochemical reaction to produce electric power and heat. In that case, for an efficient electrochemical reaction, it may be important that the fuel cell and the oxidant gas are humidified, and the anode electrode 12A and the cathode electrode 12C are maintained at a predetermined water retention state, because the reaction products move through water. Humidity may appropriately be adjusted depending on the structure or specification of the fuel cell 5.

Additionally, although the fuel gas flow channels 21A are provided on the anode separator 20A in this embodiment, the disclosure is not limited to such a structure. For example, fuel gas flow channels 21A may be provided on the anode gas diffusion layer 14A. In that case, the anode separator 20A may be formed in a planar shape.

In the same manner, although the oxidant gas flow channels 21C are provided on the cathode separator 20C in this embodiment, the disclosure is not limited to such a structure. For example, oxidant gas flow channels 21C may be provided on the cathode gas diffusion layer 14C. In that case, the cathode separator 20C may be formed in a planar shape.

Another anode separator seal 15A that serves as a sealing material is placed between the anode separator 20A and the polymer electrolyte membrane 11 so as to cover lateral surfaces of the anode catalyst layer 13A and the anode gas diffusion layer 14A, in order to prevent the fuel gas from leaking to the outside.

Furthermore, another cathode separator seal 15C that serves as a sealing material is placed between the cathode separator 20C and the polymer electrolyte membrane 11 so as to cover lateral surfaces of the cathode catalyst layer 13C and the cathode gas diffusion layer 14C, in order to prevent the oxidant gas from leaking to the outside.

Common thermoplastic resins, thermosetting resins, etc. can be employed as materials for the anode separator seal 15A and the cathode separator seal 15C. As materials for the anode separator seal 15A and the cathode separator seal 15C, silicon resins, epoxy resins, melamine resins, polyurethane-type resins, polyimide-type resins, acrylic resins, ABS resins, polypropylene, liquid crystalline polymers, polyphenylene sulfide resins, polysulfone, glass-fiber reinforced resins, etc. can be employed.

Additionally, parts of the anode separator seal 15A and the cathode separator seal 15C are preferably penetrated into peripheral parts of the anode gas diffusion layer 14A and the cathode gas diffusion layer 14C, respectively. According to such a configuration, power generation durability and the mechanical strength can be improved.

Accordingly, it becomes possible to suppress deteriorations of the polymer electrolyte membrane 11, improve handling properties of the membrane electrode assembly 10, and improve workability in large-scale production.

For a catalyst used in the anode catalyst layer 13A and/or the cathode catalyst layer 13C provided in the anode electrode 12A and the cathode electrode 12C in the structure of the fuel cell 5, a platinum group metal particle-supported catalyst (hereinafter, referred to as catalyst) according to the disclosure is employed.

<Method for Producing a Catalyst>

Figure 3:
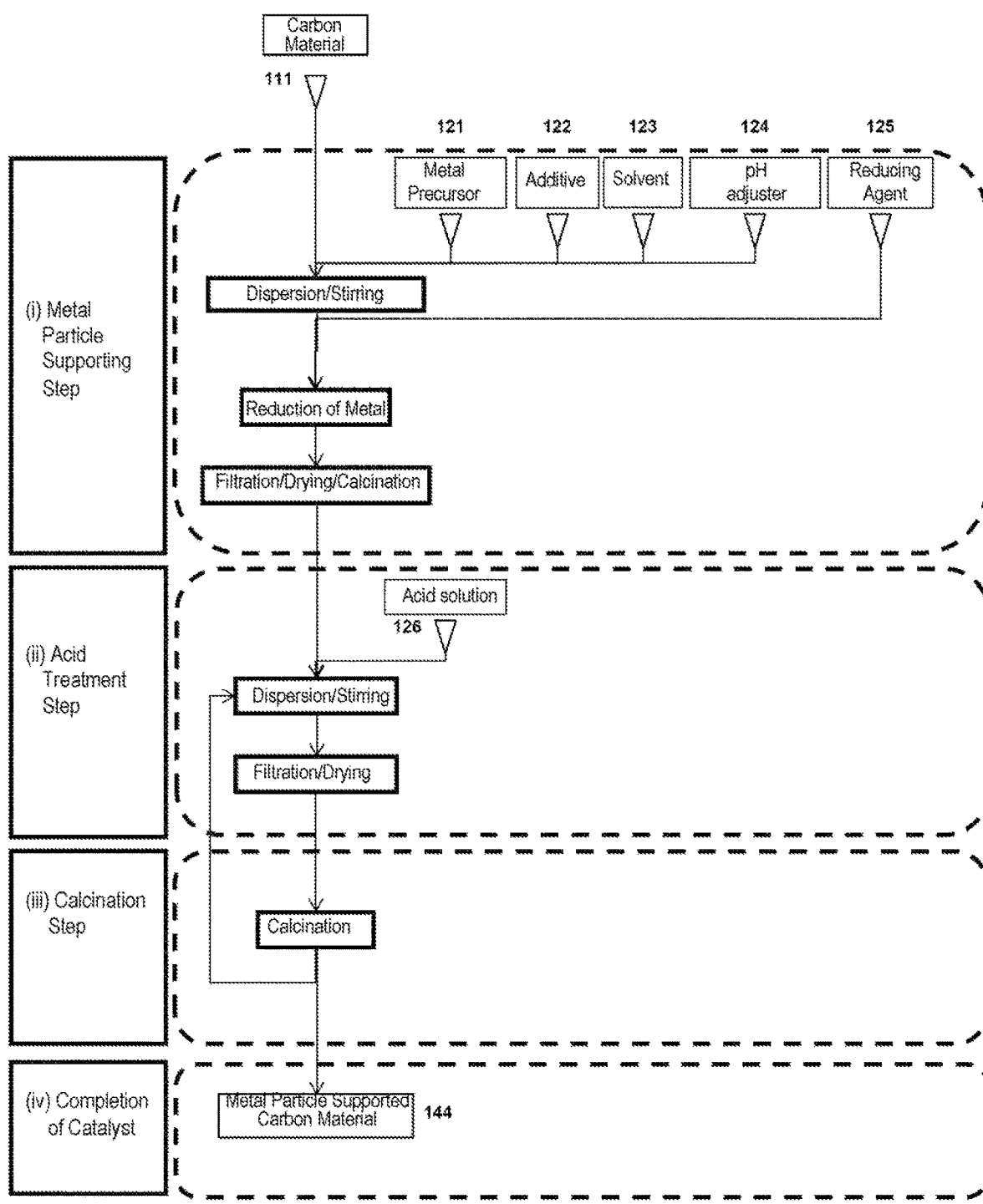
FIG. 3 is a process flowchart of a catalyst synthesis according to an embodiment.

A method for producing a catalyst according to one embodiment will be described with reference to FIG. 3.

(i) Metal Particle Supporting Step:

Metal particles at least containing platinum are supported onto a carbon material.

(ii) Acid Treatment Step:

The carbon material onto which the metal particles have been supported is soaked in an acid solution to introduce functional groups into the surface of the carbon material. In this case, single carbon-carbon bonds or double carbon-carbon bonds that form the carbon support are oxidatively cleaved by the acid solution, and thus, functional groups are formed thereon. The produced functional groups refer to hydrophilic functional groups having: oxygen atoms (e.g., carboxyl groups, hydroxyl groups, aldehyde groups, and lactone groups).

(iii) Calcination Step:

The metal particle supported carbon material 144 that has been subjected to the acid treatment is calcined at a predetermined temperature. Although changes in the functional groups have not yet been explained in detail, the following changes have been presumed. That is, all or some of the functional groups that have been introduced into the surface of the carbon material in the acid treatment step are eliminated by the heat treatment. It is considered that this elimination process results in reconstitution of molecules of the functional groups, and they are converted into new stable functional groups.

As described above, the metal particle supporting step, the acid treatment step, and the calcination step are conducted in this order.

Each of the above-mentioned steps will be described below in detail. In particular, details about an embodiment in which platinum particles serving as the metal particles are supported onto the carbon support will be described. However, contents described in the present embodiment can also be applied to any types of metals other than platinum to form particles of alloys or core-shell structures. Thus, the disclosure is not particularly limited. In that case, the core-shell structures refer to structures in which, for example, any metals other than platinum are employed as cores, and the cores are covered with a metal having catalytic activity (e.g., platinum).

[(i) Metal Particle Supporting Step]

A carbon material 111, a metal precursor 121 that serves as a material for the metal particles, and an additive 122 as needed are mixed/dispersed into a solvent 123, and the resulting mixture is stirred at a predetermined temperature for a predetermined period of time.

Additionally, while the solution is stirred, the pH of the solution was adjusted within a range of 4 to 10 by use of a pH adjuster 124, and the temperature was maintained at 30° C. to 40° C. In that case, the pH range is not particularly limited, and the pH adjustment is carried out to control zeta potential of the surface of the carbon material 111, and solubility of the metal precursor 121, for the purpose of uniformly dispersing/dissolving the carbon material 111 and the metal precursor 121. Therefore, it is required that the pH is adjusted depending on types of materials used therein.

Then, a reducing agent 125 is added to the solution to reduce metal ions that constitute the metal precursor 121. Accordingly, metal particles are supported onto the carbon material 111. Subsequently, the solution is subjected to separation based on filtration, washing, drying, and calcination. Thus, a metal particle supported carbon material 144 is extracted from the solution, and the solvent adhering to the surface of the material, and impurities adhering thereto through the previous steps are removed. These procedures of washing, drying, and calcination may be carried out based on common techniques, and are not particularly limited.

Each of the materials employed in the metal particle supporting step will be described below in details.

[Carbon Material 111]

For the carbon material 111, at least one or more materials selected from among carbon black, graphite, graphene, carbon nanotubes, and carbon fibers may be used. Among others, carbon black is preferably used therefor.

The carbon material 111 is dispersed into a predetermined solvent to prepare a carbon powder dispersion.

[Metal Precursor 121]

In this embodiment, a platinum group metal particle supported catalyst in which platinum group metal particles are used as the metal particles is produced. As examples of metal precursors 121 therefor, platinum group inorganic compounds (e.g., oxides, nitrates, and sulfates of platinum group metals), halides (e.g., chlorides of platinum group metals), organic acid salts (e.g., acetates of platinum group metals), complex salts (e.g., ammine complexes of platinum group metals), and organometallic compounds (e.g., acetylacetonato complexes of platinum group metals) can be used. Additionally, platinum group metals themselves may be dissolved in the reaction solution. In addition, the platinum group metals include elements such as Ru, Rh, Pd, Os, and Ir, beside Pt, as is commonly known.

Among others, as the platinum group salt, inorganic compounds containing platinum group metals, halides of platinum group metals, or organometallic compounds containing platinum, group metals are preferably used. More specifically, chlorides of platinum groups metals are particularly preferably used.

In addition, one type of a platinum group salt may singularly be used, or two or more types of platinum group salts may be combined at any ratio.

In the present embodiment, the above-mentioned metal precursor 121 is dissolved in a predetermined solvent to prepare a solution of a platinum group salt.

[Additive 122]

Next, the additive 122 will be described. The additive 122 may be used in order to uniformly disperse/dissolve the carbon material 111 and the metal precursor 121 into a solvent. Therefore, it required that the additive 122 is selected so as to satisfy the following conditions; the additive 122 itself is dissolved or dispersed into the solvent, does not impede dissolution of the metal precursor 121 into the solvent 123, improves affinity of the carbon material 111 for the solvent 123, and does not cause the metal particles or the carbon material 111 to aggregate in subsequent steps.

As long as the above-mentioned conditions are satisfied, additives such as common complexing agents, dispersing agents, and surfactants can be used for the additive 122. As examples of complexing agents, compounds containing a nitrogen or oxygen atom, such as ethylenediamine (abbr. EDA) (molecular formula: $H_2N(CH_2)_2NH_2$), or diethanolamine (abbr. DEA) (molecular formula: $(-HOCH_2CH_2)_2NH$), are preferable. Furthermore, as examples of surfactants, compounds including a hydrophilic amino group and a hydrophobic hydrocarbon, such as hexadecyltrimethylammonium bromide (abbr. CTAB) (molecular formula: $CH_3(CH_2)15N(CH_3)_3Br$), are preferable. In addition, compounds that combines properties of complexing agents and surfactants can also be used. However, in that case, types of complexing agents and surfactants are not limited.

[Solvent 123]

A type of the solvent 123 is not particularly limited as long as the objects of the disclosure are achieved, and expected advantages are ensured. In general, water or organic solvents may be used. As examples of organic solvents, alcohols such as methanol, ethanol, 1-propanol, and 2-propanol can be used.

Among others, water is preferably used, and distilled water or ion-exchange water is particularly preferably used, for the solvent 123, since it becomes easier to control the pH.

Additionally, for the solvent 123, any one type of a material may be used singularly, or any two or more types of materials may be combined at a predetermined ratio. However, with regard to a mixing ratio of water and alcohols, a mixing volume of alcohols is preferably 50% or less with respect to the total volume in view of control of the pH.

[pH Adjuster 124]

Subsequently, the above-described mixture solution obtained by dissolving/dispersing the metal precursor 121, the carbon material 111, and the additive 122 into the solvent 123 was subjected to pH adjustment by use of the pH adjuster 124. Surfaces of the fine particles present in the solution are charged, and, in general, their charges depend on the pH. Therefore, the charges are varied within a range of plus, 0, and minus. If the charges are around 0, the carbon material 111 will aggregate. Consequently, there is a concern that locations of the carbon material 111 where the metal particles are supported in the subsequent step would be biased.

In that case, the pH is adjusted, preferably to an acidic or alkaline region to prevent aggregation of the carbon material 111.

Furthermore, although a technique for adjusting the pH is not particularly limited, in general, a pH adjuster 124 is used. As examples of the pH adjuster 124, nitric acid, sulfuric acid, hydrochloric acid, ammonia, potassium hydroxide, and sodium hydroxide can be used. Among others, hydrochloric acid, nitric acid, and sodium hydroxide are preferable. In addition, for the pH adjuster 124, any one type of a material may be used singularly, or any two or more types of materials may be combined at a predetermined ratio.

[Reducing Agent 125]

A type of the reducing agent 125 is not limited as long as it is soluble in the solvent in which the metal precursor 121 and the carbon material 111 are dissolved/dispersed.

As specific examples of the reducing agent 125, nitrogen compounds such as hydrazine, boron compounds such as sodium borohydride, aldehydes such as formaldehyde, L-ascorbic acid and similar carboxylic acids, and alcohols such as methanol can be used.

Among others, for the reducing agent 125, sodium borohydride and hydrazine are preferable.

In addition, for the reducing agent 125, any one type of the above-mentioned materials may be used singularly, or any two or more types thereof may be combined at a predetermined ratio.

An amount of the reducing agent 125 added to the solution is preferably an amount that makes it possible to sufficiently reduce all of platinum group metal complexes (metal precursor 121) contained in the above platinum group metal salt solution to platinum group metals (metals).

In general, one or more equivalents of the reducing agent 125 would be sufficient with respect to one equivalent of the metal precursor 121. In view of sufficient efficiencies of the reduction, preferably 1.2 equivalents or higher, more preferably 1.5 equivalents or higher, still mere preferably 2 equivalents or higher of the reducing agent 125 may be added to the solution with respect to one equivalent of the metal precursor 121.

Moreover, in consideration of e.g. posttreatments to unreacted metal precursor 121, in general, the upper limit of the amount of the reducing agent 125 may be preferably 500 equivalents or lower, more preferably 100 equivalents or lower, particularly preferably 40 equivalents or less with respect to one equivalent of the metal precursor 121.

Furthermore, a method for bringing the platinum group metal salt solution, the carbon powder dispersion, and the reducing agent 125 into contact with each other is not particularly limited.

In general, the reducing agent 125 may be mixed into a mixture of the above platinum group metal salt solution and the above carbon powder dispersion to carry out a reduction of the platinum group metal.

In addition, although the reducing agent 125 can be mixed directly into the platinum group metal salt solution, the reducing agent 125 may be dissolved into a solvent in advance, and the resulting solution (hereinafter, referred to as "reducing agent solution") may be mixed into the platinum group metal salt solution, in order to facilitate mixing/dissolution of the reducing agent 125 into the platinum group metal salt solution.

In that case, the type of solvent is not particularly limited as long as the solvent makes it possible to dissolve the reducing agent 125. Additionally, one type of solvent may be used singularly, or any two or more types of solvents may be combined at a predetermined ratio. However, in general, the same solvent used for the platinum group metal salt solution may be used therefor.

A concentration of the reducing agent 125, or an amount of the reducing agent solution are also not particularly limited. The concentration or the amount may appropriately be adjusted such that, when the reducing agent solution is added to the platinum group metal salt solution, a proportion of the reducing agent 125 to metals present in the platinum group metal salt solution satisfies the above-mentioned conditions.

A temperature for the reduction is typically 4° C. or higher, preferably 10° C. or higher, and is typically equal to or lower than the boiling point, preferably 95° C. or lower, more preferably 90° C. or lower. If the temperature for the reduction is excessively high, the reduction proceeds faster, and therefore, products other than objective platinum group compounds may be produced. On the other hand, if the temperature is excessively low, the reducing capacity may become excessively low, and therefore, it may be impossible to obtain objective platinum group compounds.

In addition, as examples of procedures for initiating the reduction, the following methods (1) and (2) can be used. However, any procedures can be employed therefor.

(I) The first, method is a technique in which the reducing agent 125 (reducing agent solution) is added to the mixture of the platinum group metal salt solution and the carbon powder dispersion, at a temperature where the reduction does not proceed even when the reducing agent 125 is added to the solution, i.e., a temperature lower than the above-defined temperature ranges for the reduction, typically at ordinary temperature or a temperature lower than ordinary temperature, preferably 10° C. or lower, more preferably 5° C. or lower, followed by mixing, and then, the mixture is heated to a temperature sufficient to cause the reduction to proceed (e.g., a temperature falling within the above-defined temperature ranges).

(II) The second method is a technique in which the mixture of the platinum group metal salt solution and the carbon powder dispersion is preliminarily heated to a temperature that causes a reduction of the platinum group metal salt to sufficiently proceed, i.e., a temperature falling within the above-defined temperature ranges, and then, the reducing agent 125 is added to the mixture solution in that state to initiate the reduction reaction.

Through the prior steps, a solution in which the metal particle supported carbon material 144, which has been formed by supporting metal particles onto the carbon material 111, is dispersed can be produced. The dispersed metal particle supported carbon material 144 is separated by filtration, and is sufficiently washed with water, ethanol or the like. This washing step may be finished when it is confirmed that the filtrate is no longer alkaline and sufficiently neutral.

Additionally, in order to remove solvents remaining on the metal particle supported carbon material 144 that has been separated by filtration, the metal particle supported carbon material 144 may be dried at 50° C. to 110° C., or may be allowed to stand under reduced-pressure atmosphere. Furthermore, in cases in which remnants such as complexing agents and/or surfactants remain thereon, the separated metal particle supported carbon material 144 may be calcined at 100° C. to 400° C. to remove them, as needed.

[(ii) Acid Treatment Step]

The metal particle supported carbon material 144 that has been separated by filtration in the metal particle supporting step may be added to at least one acid solution 126 selected from among nitric acid, sulfuric acid, and hydrochloric acid, to thereby adjust the pH of the resulting mixture solution to 1 to 2.

Additionally, the concentration of the acid may be set to 0.5 to 3 mol/L, the temperature may be set to 30° C. to 80° C., and the mixture solution may be stirred for 0.5 to 12 hours. Then, the metal particle supported carbon material 144 may be separated by filtration, and may sufficiently be washed with pure water. In that case, in the washing manipulation, by use of a pH meter or pH test strip, it may be confirmed that the filtrate is no longer acidic but sufficiently neutral. Then, the metal particle supported carbon material 144 separated by filtration may be dried at 100° C. or lower, or may be allowed to stand under pressure-reduced atmosphere, to remove the solvent.

[(iii) Calcination Step]

The metal particle supported carbon material 144 that has been subjected to the above-described acid treatment step may be calcined in an inert gas such as a nitrogen or argon gas, or a reducing gas produced by adding hydrogen to an inert gas. In that case, the calcination temperature may be set to 150° C. to 300° C.

[(iv) Perfection of Catalyst]

Through the above-described metal particle supporting step (i), acid treatment step (ii), and calcination step (iii), the metal particle supported carbon material 144 is obtained.

Examples

With regard, to the above-described embodiments of the disclosure, working examples and comparative examples will be shown below.

At first, general procedures, conditions, etc. adopted for the working examples will be described.

(i) Metal Particle Supporting Step

First, Ketjenblack EC series (manufactured by LION CORPORATION), which are carbon materials having large surface areas, were used as carbon materials 111.

The surface areas of the carbon materials 111 were from 600 to 1000 $m^2/g$. In addition, in accordance with the evaluation method described in JP-A-2012-129059, volumes of pores of 10 nm or smaller are considered to be 0.6 $cm^3/g$ or larger.

Next, hydrogen hexachloroplatinate (IV) hexahydrate ($H_2PtCl_6 \cdot 6H_2O$) was used as a metal precursor 121, and ethylene diamine was used as a complexing agent for the additive 122. Mixing ratios of the metal precursor 121 and the additive 122 were from 1:2 to 1:10 in terms of molar ratio, and they were dissolved in aqueous ethanol solutions (solvent 123) (water:ethanol=1:0.1 to 1:0.4). The solutions were heated and stirred at 3° C. to 50° C. for 12 to 24 hours. In that case, in order to improve dispersibility of the carbon materials 111, it may be possible to add a surfactant to the solution. In addition, by using nitric acid and sodium hydroxide as a pH adjuster 124, the solutions were adjusted so as to be maintained at a predetermined pH.

Then, hydrazine was added to the above stirred solutions, and the mixture solutions were stirred for predetermined periods of time. In this way, platinum was reduced so as to support metal particles onto the carbon materials 111, and thus, the metal particle supported carbon materials 144 were produced in the solutions. Then, through separation by filtration, washing, and drying, the metal particle supported carbon materials 144 were obtained.

(ii) Acid Treatment Step

Next, the above metal particle supported carbon materials 144 were added to aqueous nitric acid solutions with concentrations of 0.5 to 3 mol/L, and the mixture solutions were stirred for 0.5 to 3 hours while the solutions were heated to 80° C. After stirring the solutions, the solutions were filtrated to separate the metal particle supported carbon materials 144, which have been subjected to the acid treatment step, and the separated metal particle supported carbon materials 144 were washed with sufficient amounts of pure water. In this step, it is required that the metal particle supported carbon materials 144 be washed until the pH of the filtrates become neutral. If large amounts of nitric acid remain thereon, properties of the catalysts may be influenced. Water was removed from the metal particle supported carbon materials 144 by filtration, under reduced-pressure atmosphere. Thus, the metal particle supported carbon materials 144 were dried.

It may be undesirable that the concentration of the aqueous nitric acid solution is set to 0.5 mol/L or less, because it may become difficult to provide the metal particle supported carbon materials 144 with functional groups. Additionally, if the concentration is set to 3 mol/L or higher, the concentration may be excessively high, and thus, the surfaces of the carbon materials 111 may be corroded. Since it may be undesirable in view of costs and safeness that the concentration is adjusted to be higher, the concentration was adjusted to 0.5 to 3 mol/L in the examples.

Furthermore, with regard to the temperature and the time for the nitric acid treatment, the treatment time can be shortened as the temperature becomes higher. The temperature and the time are not particularly limited, and would be adjusted within appropriate ranges.

(iii) Calcination Step

Next, the obtained metal particle supported carbon materials 144 were calcined at 150° C. to 300° C. in an argon atmosphere containing 2% to 5% of hydrogen, for 0.5 to 3 hours.

Additionally, the nitric acid treatment and the calcination treatment were repeated at predetermined numbers of times so as to increase amounts of functional groups provided on the carbon materials 111.

According to the calcination step, some of functional groups that have been formed by weak bonds will be removed. Therefore, it is considered that functional groups that have not been removed through the calcination step are provided on the carbon material based on strong bonds. Consequently, few functional groups that have remained on the surface of the carbon material 111 after the calcination step are eliminated through the subsequent nitric acid treatment, and it is considered that, by repeating the nitric acid treatment and the calcination treatment at predetermined numbers of times, the amounts of functional groups provided onto the carbon materials 111 can be increased.

<Evaluation Criteria>
[Measurement of Amounts of Functional Groups Present on Carbon Materials]

A method for evaluating amounts of functional groups present on carbon materials 111 will be described below.

As species of functional groups on carbon materials 111, carboxyl groups, hydroxyl groups, aldehyde groups, ketone groups, quinone groups, lactone groups, etc. would be present. These species are functional groups containing oxygen atoms. Therefore, molecular states of carbon atoms and oxygen atoms were measured based on IR.

Peaks derived from the above-mentioned functional groups were extracted from the obtained IR spectra, and amounts of the functional groups were calculated from spectrum intensities (areas).

As mentioned in the above section of embodiments of the disclosure, proportions of carboxyl groups to total amounts of functional groups were calculated.

For methods for measuring amounts of functional groups present on carbon materials, techniques based on XPS or acid-base titration are known. However, the method, used in the disclosure is not particularly limited.

[Preparation of Fuel Cells for Evaluations]

Power generation evaluation apparatuses each including the structure of the fuel cell 5 shown in FIG. 2 were employed. A method for producing the membrane electrode assembly 10 included therein will be described.

Specifically, catalysts according present embodiments were used for the cathode, electrode 12C to form fuel cells, and power generation properties of the prepared fuel cells are evaluated. For preparation of the cathode electrodes 12C, catalysts prepared in comparative examples, and working examples according to the disclosure, were dispersed in solvents obtained by mixing ethyl alcohol and water at predetermined ratios, or solvents obtained by mixing 2-propanol, n-propanol, and water at predetermined ratios. They were dispersed based on ultrasound exposure, as needed.

Then, predetermined amounts of 5% ionomer solutions were added to the resulting dispersions, and the mixtures were stirred.

The amounts of the ionomers were adjusted so as to be 0.5 to 0.9 equivalent to amounts of carbon materials that constituted the catalysts.

Then, the resulting mixture solutions were coated onto electrolyte membranes by spraying, such that, amounts of platinum were adjusted to be at 0.2 to 0.3 mg/cm$^2$, thereby forming coated membranes.

Then, the coated membranes were subjected to hot pressing at 130° C. to 150° C. and at 5 to 30 kg/cm$^2$ to prepare cathode electrodes.

Anode electrodes 12A were prepared by using TEC10E50E (TANAKA KIKIHZOKU KOGYO K.K.), which is an anode standard catalyst, in the same manner as the above-described method for producing cathode electrodes 12C.

The produced membrane-electrode assemblies 10 were used to prepare fuel cells, and power generation properties of the prepared fuel cells (examples and comparative examples) were evaluated based on the following conditions.

[Conditions for Evaluations on Power Generation Properties of Fuel Cells]

For evaluations on power generation properties of the membrane-electrode assemblies 10, electric power generation was carried out under conditions where the cell temperature was set to 80° C., dew-point temperatures of cathodes and anodes were set to 65%, utilization rates of oxygen and hydrogen were set to 50% to 70%, and current densities were set to 0.25 A/cm$^2$, and voltages were measured during the electric power generation. The reason why the current densities were set to 0.25 A/cm$^2$ is because such a value is equivalent to a current density used for household fuel cells. However, current densities adopted in the disclosure are not particularly limited.

[Evaluations on Proton Conduction Overvoltages]

To realize power generation, in fuel cells, conduction of hydrogen ions (protons) is required. Decrements of voltage caused by such conduction of protons are referred to as proton conduction overvoltages.

Proton conduction overvoltages were calculated based on Formula 1.

$$\text{Proton conduction overvoltage} = \text{total overvoltage} - \text{resistance overvoltage} - \text{active overvoltage} \quad \text{(Formula 1)}$$

The total overvoltage, the resistance overvoltage, and the active overvoltage were calculated based on the following ways.

The total overvoltage refers to a difference between a theoretically output power generation voltage and an actual power generation voltage.

With regard to the total overvoltage, voltages were obtained for the above-described cells for the fuel cells based on the above-described conditions for evaluations on power generation properties, and differences between the obtained voltages and 1.2 V, which is a theoretically output power generation voltage, were considered as total overvoltages.

The resistance overvoltage refers to a decrement of voltage caused by a resistance component in the thickness direction in a stack structure including the polymer electrolyte membrane and catalyst layers that constitute the fuel cell. In this case, a resistance value was measured at a current density of 0.25 A/cm², and the resistance overvoltage was calculated as a product of the measured resistance value and the current value.

When a reaction gas is supplied to the fuel cell, voltage is formed between the anode electrode and the cathode electrode. From that state, by providing a load resistor between the anode electrode and the cathode electrode, the fuel cell is looped, and thus, a certain current flows therethrough. A decrement of voltage in that case is referred to as an active overvoltage.

The active overvoltages were calculated in the following way. First, a voltage is obtained at a current density of 0.06 A/cm². Next, assuming that the current density drops by 70 mV when the current density changes by 10 times, the voltage at the current density of 0.25 mA/cm 2 was calculated and the difference from 1.2 V was calculated. In addition, this evaluation method was decided independently. The value of the active overvoltages can be used as a relative evaluation.

Samples of metal particle supported carbon materials 144 were prepared based on the above-described method for producing a catalyst while conditions for the acid treatment step and the calcination step were varied, and the prepared samples were evaluated for amounts of functional groups, and proton conduction overvoltages.

When samples exhibited proton conduction overvoltages higher than 35 mV, they were graded as inferior. When samples exhibited proton conduction overvoltages higher than 30 mV but less than or equal to 35 mv, they were graded as fair. When samples exhibited proton conduction overvoltages less than or equal to 30 mV, the samples were graded as excellent. Effects to reduce the proton conduction overvoltage can be obtained even for the samples graded as fair. However, decrements of the overvoltage observed in the samples were small. In order to realize lower proton conduction overvoltages, it is considered that conditions (i.e., less than or equal to 30 mV) for the samples graded as excellent are preferable.

A reason why 30 mV was adopted as a threshold is because, when the proton conduction overvoltage is less than or equal to 30 mV, the produced fuel cell causes little loss in power generation, and is easily commercialized.

Results of evaluations on comparative example 1, and examples 1 to 6, and conditions adopted in these examples are summarized in Table 1, and will be explained below.

Example 2

A catalyst, and a fuel cell were prepared in the same manner as EXAMPLE 1 except that the acid treatment step was conducted three times, and the calcination step was not carried out.

Example 3

A catalyst, and a fuel cell were prepared in the same manner as EXAMPLE 1 except that one round of the acid treatment step and the calcination step was conducted. Note that, in one round, the acid treatment was conducted one time, and the calcination step was conducted one time, and the same shall apply to the other examples.

Example 4

A catalyst, and a fuel cell were prepared in the same manner as EXAMPLE 1 except that two rounds of the acid treatment and the calcination step were conducted.

Example 5

A catalyst, and a fuel cell were prepared in the same manner as EXAMPLE 1 except that three rounds of the acid treatment and the calcination step were conducted.

Example 6

A catalyst, and a fuel cell were prepared in the same manner as EXAMPLE 1 except that five rounds of the acid treatment and the calcination step were conducted.

<Modification of EW Values of Ionomer>

Next, in EXAMPLES 7 to 11, a series of catalysts were prepared based on the production method according to the disclosure in which the acid treatment step and the calcination step were carried out under the same conditions, while ionomers having different EW values were employed. These catalysts were used to prepare fuel cells, and the fuel cells were evaluated in terms of proton conduction overvoltage. The conditions and results for EXAMPLES 7 to 11 are summarized in Table 2.

TABLE 1

|  | COMPARATIVE EXAMPLE 1 | EXAMPLE 1 | EXAMPLE 2 | EXAMPLE 3 | EXAMPLE 4 | EXAMPLE 5 | EXAMPLE 6 |
|---|---|---|---|---|---|---|---|
| (A) Acid treatment step | — | Yes | Yes | Yes | Yes | Yes | Yes |
| (B) Calcination step after acid treatment step | — | No | No | Yes | Yes | Yes | Yes |
| Repeating times of (A) and (B) | — | 1 | 3 | 1 | 2 | 3 | 5 |
| Proportions of carboxyl groups to total amounts of functional groups | 0.08 | 0.14 | 0.14 | 0.17 | 0.19 | 0.18 | 0.22 |
| Proton conduction overvoltage (mV) | 36 | 31 | 31 | 30 | 27 | 18 | 15 |
| Acceptance | Inferior | Fair | Fair | Excellent | Excellent | Excellent | Excellent |

<With Regard to Proportions of Carboxyl Groups>

Example 1

In accordance with the above-described procedures and conditions, a catalyst, and a fuel cell were prepared. The acid treatment step was carried out one time, and the calcination step was not carried out.

Additionally, the ionomers used in these working examples were fluorinated sulfonic acid resins. EW (Equivalent Weight) values refer to dry weights of ionomers per one mole of sulfonic acid group. The smaller the value is, the larger the proportion of sulfonic acid groups is.

The EW values can also be used even when ionomers other than fluorinated sulfonic resins are employed, and, in that case, the values refer to dry weights of the ionomers per one mole of ionic groups other than sulfonic groups.

Additionally, in these examples, proton conduction overvoltages were reduced.

TABLE 2

|  | EXAMPLE 7 | EXAMPLE 8 | EXAMPLE 9 | EXAMPLE 10 | EXAMPLE 11 |
|---|---|---|---|---|---|
| (A) Acid treatment step | Yes | Yes | Yes | Yes | Yes |
| (B) Calcination step after acid treatment step | Yes | Yes | Yes | Yes | Yes |
| Repeating times of (A) and (B) | 3 | 3 | 3 | 3 | 3 |
| Proportions of carboxyl groups to total amounts of functional groups | 0.18 | 0.18 | 0.18 | 0.18 | 0.18 |
| EW | 1500 | 1300 | 1000 | 700 | 500 |
| Proton conduction overvoltage (mV) | 40 | 25 | 20 | 16 | 15 |

Example 7

A catalyst, and a fuel cell were prepared in the same manner as EXAMPLE 1 except that three rounds of the acid treatment and the calcination step were conducted, and that an ionomer having an EW value of 1500 was used.

Example 8

A catalyst, and a fuel cell were prepared in the same manner as EXAMPLE 1 except that three rounds of the acid treatment and the calcination step were conducted, and that an ionomer having an EW value of 1300 was used.

Example 9

A catalyst, and a fuel cell were prepared in the same manner as EXAMPLE 1 except that three rounds of the acid treatment and the calcination step were conducted, and that an ionomer having an EW value of 1000 was used.

Example 10

A catalyst, and a fuel cell were prepared in the same manner as EXAMPLE 1 except that three rounds of the acid treatment and the calcination step were conducted, and that an ionomer having an EW value of 700 was used.

Example 11

A catalyst, and a fuel cell were prepared in the same manner as EXAMPLE 1 except that three rounds of the acid treatment and the calcination step were conducted, and that an ionomer having an EW value of 500 was used.

<Results and Discussion>
<Proportion of Carboxyl Groups to Total Amounts of Functional Groups>

It would be realized that, in COMPARATIVE EXAMPLE 1, the proportion of carboxyl groups to the total amount of functional groups is smaller, and the proton conduction overvoltage is higher.

In EXAMPLES 1 and 2, since acid treatment step was carried out, proportions of carboxyl groups to total amounts of functional groups tended to increase, while a reduction in proton conduction overvoltages were observed.

Furthermore, in EXAMPLES 3 to 6, after the acid treatment and the calcination steps were carried out, the proportions of carboxyl groups to total amounts of functional groups were increased.

Figure 4:
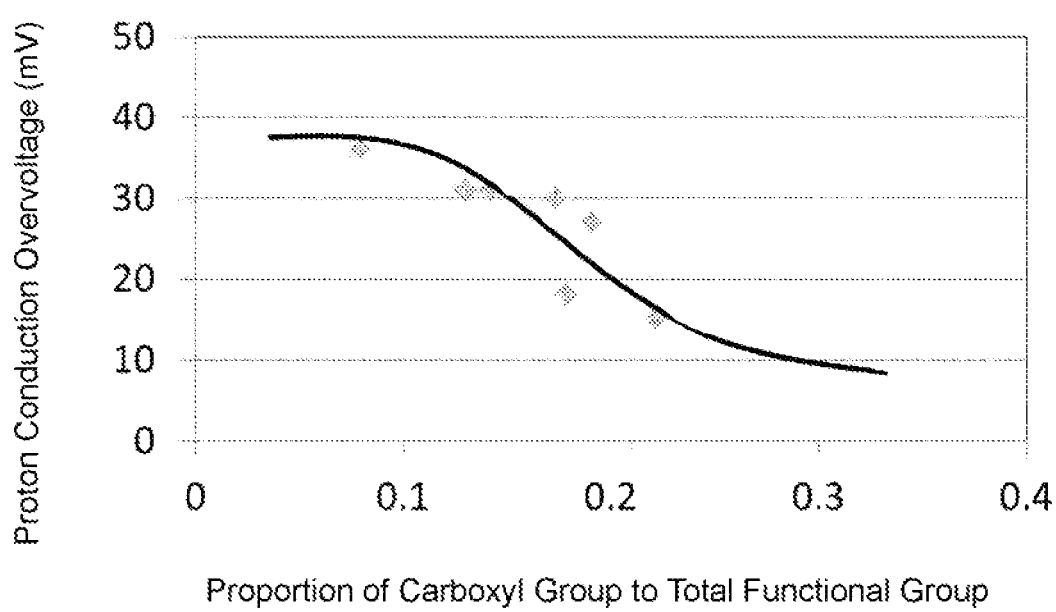
FIG. 4 is a diagram that shows relations between a proportion of a certain functional group and proton conduction overvoltages in an embodiment.

A graph showing relations between proportions of carboxyl groups to total amounts of functional groups and proton conduction overvoltages is shown in FIG. 4.

According to the results, proton conduction overvoltages are frequently reduced when the proportions of carboxyl groups to total amounts of functional groups are higher than or equal to 0.1 (10%). Furthermore, there is a tendency that proton conduction overvoltages are drastically decreased when the proportions of carboxyl groups to total amounts of functional groups are higher than or equal to 0.15 (15%). According to FIG. 4, 10% can be considered as a critical point where the proton conduction overvoltages are drastically decreased.

Based on the results, the proportions of carboxyl groups to total amounts of functional groups are adjusted to be preferably 0.1 or higher, more preferably 0.15 or higher. Additionally, although conditions are not particularly limited, it is difficult in practice to only provide carboxyl groups as functional groups on the carbon materials. It has experimentally been understood that other types of functional groups are produced as byproducts in the acid treatment step, and it is difficult to increase the proportions of carboxyl groups to 0.7 or higher.

Consequently, the proportion is preferably 50% or less, more preferably 30% or less. According to FIG. 4, if the proportion is higher than 30%, the proton conduction overvoltage is not sufficiently reduced.

Furthermore, if the number of times of acid treatment is excessively high, increased costs is a concern. Therefore, the proportion of carboxyl groups to the total amount of functional groups is adjusted preferably to 0.7 or smaller.

Now, a reason why the proton conduction overvoltage is reduced depending on increases in the proportion of carboxyl groups to the total amount of functional groups will be described below with reference to FIG. 5.

Figure 5:
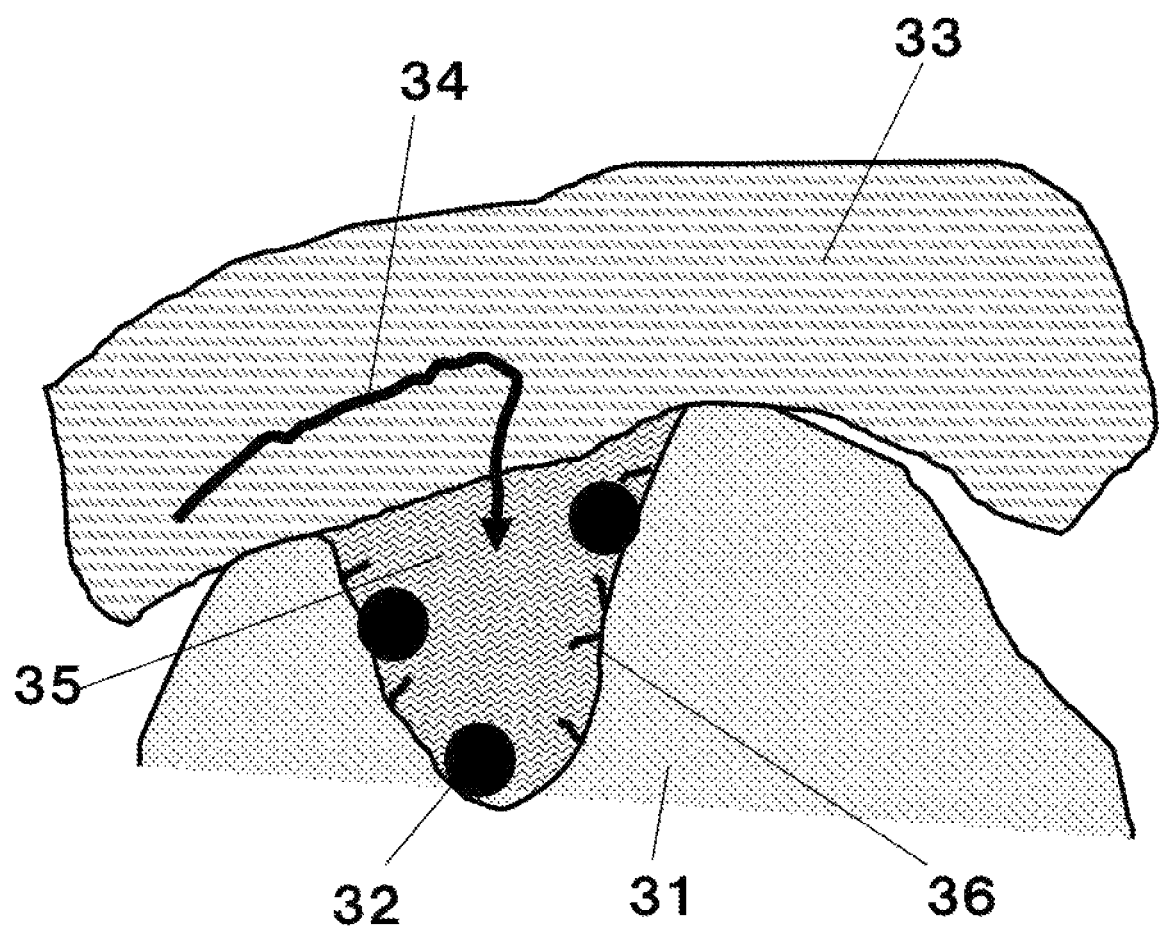
FIG. 5 is a diagram that describes advantages according to an embodiment.

FIG. 5 is a diagram that shows positional relations among the carbon support 31, the metal particles 32, and the ionomer 33, and a conduction pathway 34 through which protons conduct. Protons pass through the conduction pathway 34 within the ionomer 33, and are transmitted to areas around the metal particles 32. Then, the protons pass through water 35 retained between the ionomer 33 and the metal particles 32, and thus, are transmitted from the ionomer 33 to the metal particles 32.

Figure 6A:
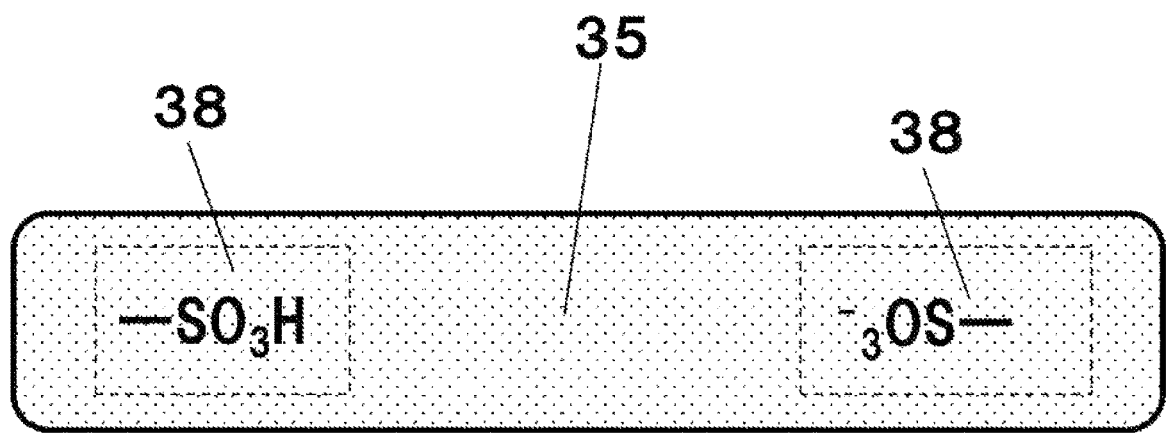
FIG. 6A is a diagram that shows a structure of a polymer that constitutes an ionomer in an embodiment.
Figure 6B:
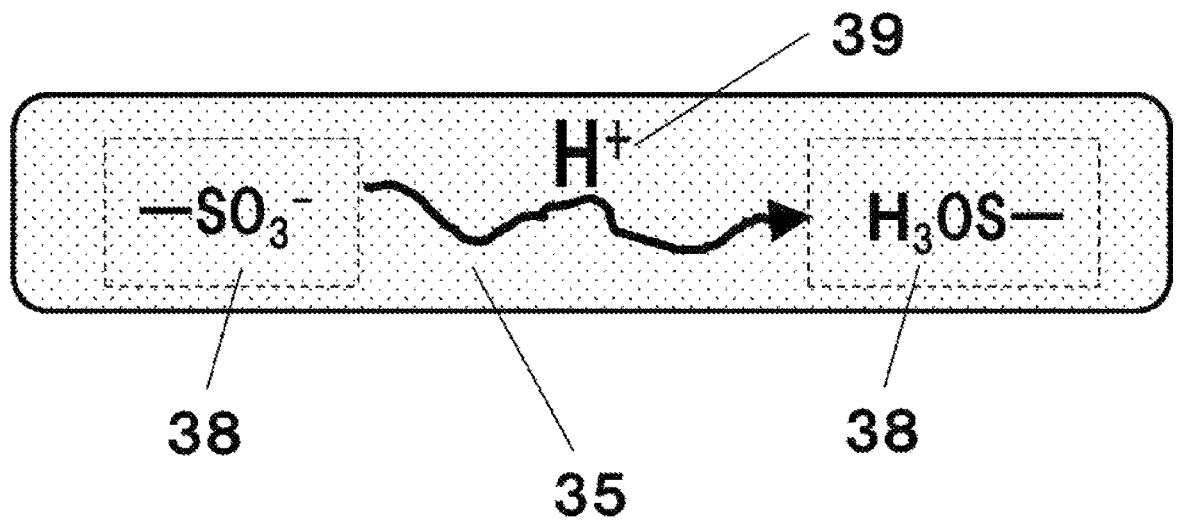
FIG. 6B is a diagram that shows conduction of protons through an ionomer in an embodiment.

Next, a mechanism for conduction of protons within the ionomer 33 will be described with reference to FIGS. 6A and 6B. A polymer constituting the ionomer 33 has acidic groups (sulfonic acid groups 38 in general) as side chains, as shown in FIG. 6A. Furthermore, the adjacent sulfonic acid groups 38 dissociate and absorb protons therebetween under conditions where water 35 exists, and thus, the proton 39 is transmitted therebetween, as shown FIG. 6B. It has been considered that protons transmit inside the ionomer based on such a conduction mechanism.

In the disclosure, functional groups 36 such as carboxyl groups that easily dissociate/absorb protons are present on irregular surfaces of the carbon support 31, as shown in FIG. 5. It is presumed that conduction of protons between the ionomer 33 and the metal particles 32 easily occurs, and this results in reductions in the proton conduction overvoltage, since such functional groups 36 facilitate conduction of protons in the same manner as the above-described conduction of protons by the ionomer.

Besides carboxyl groups, other types of functional groups such as hydroxyl groups are present as species of functional groups 36. However, other types of functional groups such as hydroxyl groups hardly dissociate protons, compared with carboxyl groups. Therefore, if the proportion of carboxyl groups is smaller than the proportion of other types of functional groups, protons dissociated from carboxyl groups will be absorbed by the other types of functional groups. That is, this impedes conduction of protons. Therefore, it is considered that an amount of carboxyl groups higher than or equal to a certain proportion needs to be present.

<EW of Ionomer>

Next, in EXAMPLE 7, since the EW value of the ionomer is higher, the proton conduction overvoltage is also higher. However, when the EW value is 1300 or less, proton conduction overvoltage frequently becomes lower, as observed in EXAMPLES 8 to 12.

Figure 7:
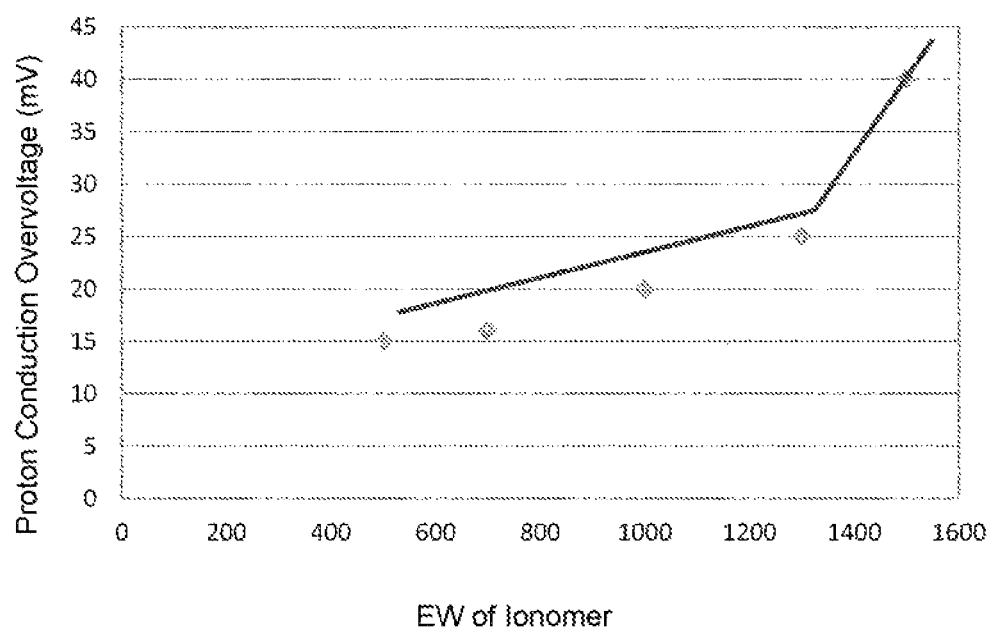
FIG. 7 is a diagram that shows relations between EW values of an ionomer and proton conduction overvoltages in an embodiment.
Figure 8A:
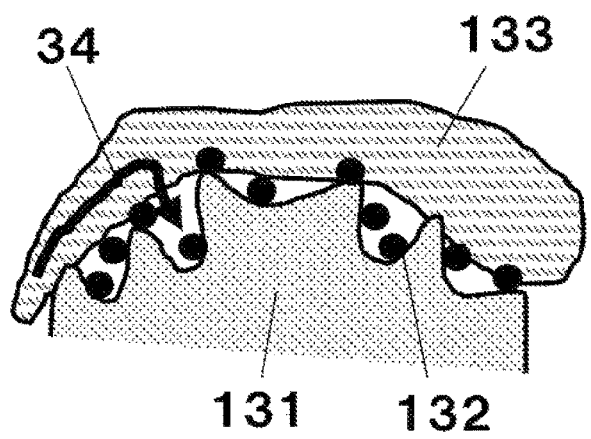
FIGS. 8A and 8B are cross-section views that show catalysts disclosed in JP-A-2012-129059.
Figure 8B:
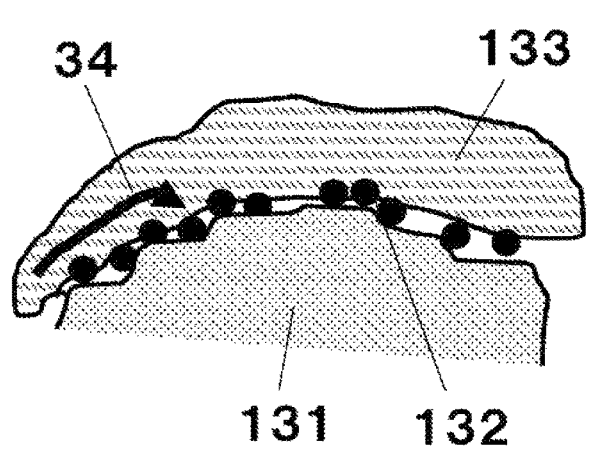

Relations between EW values of ionomers and proton conduction overvoltages are shown in FIG. 7. When EW values of ionomers are larger, i.e., when ionomers have smaller amounts of sulfonic acid groups, the ionomers themselves have inferior conduction of protons. Additionally, it is presumed that, since conduction of protons from the ionomers to the platinum particles is inferior, the proton conduction overvoltages become higher.

Even if the proportion of carboxyl groups on the carbon support is increased in that state, it is considered that it is difficult to obtain effects to reduce proton conduction overvoltage.

Furthermore, it is considered that, when EW values of ionomers are smaller, i.e., when the ionomers have larger amounts of sulfonic acid groups, proton conduction properties of ionomers themselves are enhanced, and conduction of protons between the ionomers and the platinum particles. Accordingly, it is considered that effects brought about by increases in the proportions of carboxyl groups on the carbon supports are easily obtained, and this leads to decreases in the proton conduction overvoltage.

That is, in order to reduce proton conduction voltages, it is important that catalysts that are produced based on the treatments in present disclosure and have increased proportions of carboxyl groups are employed, and they are combined with the ionomers.

According to the results, EW values of ionomers are preferably 1300 or less. Furthermore, the EW values are preferably as small as possible. However, it is difficult to produce an ionomer having an excessively small EW value due to concerns about costs. Therefore, the EW values are preferably set to 500 or higher.

Catalysts, methods for producing the same, and fuel cells using the same according to the disclosure are applicable to the fields of, for example, polymer electrolyte fuel cells, although industrial applicability of the disclosure is not particularly limited.

What is claimed is:

1. A fuel cell, comprising:
   a catalyst; and
   an electrode layer containing an ionomer,
   wherein the catalyst comprises:
      a carbon support that possesses functional groups containing oxygen; and
      a metal that is supported onto the carbon support,
      wherein the functional groups containing oxygen comprise carboxyl groups, hydroxyl groups, aldehyde groups, ketone groups, quinone groups, and lactone groups, and
      wherein the proportion of the carboxyl groups to the total amount of the functional groups containing oxygen is 15% to 30%.

2. The fuel cell according to claim 1, wherein the ionomer is a perfluorosulfonic acid ionomer, and has an EW value of 1300 or lower.

3. The fuel cell according to claim 1, wherein the proportion of the carboxyl group to the total amount of the functional groups containing oxygen is 17% to 30%.

* * * * *